US012708288B2

(12) United States Patent
Jeon et al.

(10) Patent No.: US 12,708,288 B2
(45) **Date of Patent: *Aug. 18, 2026**

(54) PORTABLE THREE-DIMENSIONAL IMAGE MEASURING DEVICE, THREE-DIMENSIONAL IMAGE MEASURING METHOD USING SAME, AND MEDICAL IMAGE MATCHING SYSTEM

(71) Applicant: KOH YOUNG TECHNOLOGY INC, Seoul (KR)

(72) Inventors: Moon Young Jeon, Seongnam-si (KR); Seung Yeol Ryu, Gunpo-si (KR)

(73) Assignee: KOH YOUNG TECHNOLOGY INC, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 19/217,381

(22) Filed: May 23, 2025

(65) Prior Publication Data

US 2025/0281069 A1 Sep. 11, 2025

Related U.S. Application Data

(63) Continuation of application No. 18/248,856, filed as application No. PCT/KR2021/014106 on Oct. 13, 2021, now Pat. No. 12,318,188.

(30) Foreign Application Priority Data

Oct. 13, 2020 (KR) ........................ 10-2020-0131843

(51) Int. Cl.
*A61B 5/107* (2006.01)
*A61B 5/00* (2006.01)
(Continued)

(52) U.S. Cl.
CPC .......... *A61B 5/1079* (2013.01); *A61B 5/0013* (2013.01); *A61B 5/0077* (2013.01);
(Continued)

(58) Field of Classification Search
CPC .... A61B 2034/2048; A61B 2034/2057; A61B 2034/2059; A61B 2034/2065;
(Continued)

(56) References Cited

U.S. PATENT DOCUMENTS 12,318,188 B2 * 6/2025 Jeon .................... A61B 5/0064
2012/0092461 A1 4/2012 Fisker et al.
(Continued)

FOREIGN PATENT DOCUMENTS

CN 1122681 5/1996
CN 101166467 4/2008
(Continued)

OTHER PUBLICATIONS

Chinese Office Action dated Dec. 10, 2025, in Chinese Patent Application No. 202180069857.7.
(Continued)

*Primary Examiner* — Michael T Rozanski
(74) *Attorney, Agent, or Firm* — KILE PARK REED & HOUTTEMAN PLLC

(57) ABSTRACT

A portable three-dimensional image measuring device according to various embodiments of the present disclosure may include a light source configured to output patterned light; a camera configured to generate a light field image of an object by receiving reflected light generated by reflecting the patterned light from the object; and an optical path control element configured to reflect the patterned light output from the light source so that the object is irradiated with the patterned light, and to transmit the reflected light reflected from the object so that the reflected light reaches
(Continued)

the camera. An optical path of the patterned light output from the light source and irradiated onto the object and an optical path of the reflected light reflected from the object and reaching the camera may overlap coaxially in a section between the optical path control element and the object.

20 Claims, 12 Drawing Sheets

(51) Int. Cl.
*A61B 5/06* (2006.01)
*A61B 90/00* (2016.01)

(52) U.S. Cl.
CPC ............ *A61B 5/065* (2013.01); *A61B 5/1077* (2013.01); *A61B 2090/364* (2016.02); *A61B 2560/0431* (2013.01); *A61B 2562/0233* (2013.01); *A61B 2576/00* (2013.01)

(58) Field of Classification Search
CPC ...... A61B 2090/309; A61B 2090/3618; A61B 2090/364; A61B 2560/0431; A61B 2562/0233; A61B 2576/00; A61B 34/20; A61B 5/0013; A61B 5/0064; A61B 5/0077; A61B 5/065; A61B 5/1075; A61B 5/1077; A61B 5/1079; A61B 90/361; G01B 11/2513
See application file for complete search history.

(56) References Cited

U.S. PATENT DOCUMENTS

| | | | |
|---|---|---|---|
| 2014/0163388 | A1 | 6/2014 | Sasayama et al. |
| 2015/0054922 | A1 | 2/2015 | Fisker et al. |
| 2015/0097931 | A1 | 4/2015 | Hatzilias et al. |
| 2018/0255293 | A1 | 9/2018 | Fisker et al. |
| 2019/0124323 | A1 | 4/2019 | Fisker et al. |
| 2019/0183583 | A1 | 6/2019 | Hong |
| 2019/0200006 | A1 | 6/2019 | Fisker et al. |
| 2019/0254783 | A1 | 8/2019 | Moon |
| 2019/0289283 | A1 | 9/2019 | Fisker et al. |
| 2019/0376784 | A1 | 12/2019 | Tewes et al. |
| 2020/0169722 | A1 | 5/2020 | Fisker et al. |
| 2020/0281660 | A1 | 9/2020 | Homan et al. |
| 2021/0211638 | A1 | 7/2021 | Fisker et al. |
| 2021/0298582 | A1 | 9/2021 | Moon |
| 2021/0306617 | A1 | 9/2021 | Fisker et al. |

FOREIGN PATENT DOCUMENTS

| | | |
|---|---|---|
| CN | 103868895 | 6/2014 |
| CN | 109475394 | 3/2019 |
| CN | 109938843 | 6/2019 |
| CN | 110720986 | 1/2020 |
| CN | 111012325 | 4/2020 |
| EP | 2 442 720 | 8/2016 |
| JP | 2001-238894 | 9/2001 |
| JP | 2010-054320 | 3/2010 |
| JP | 2012-530267 | 11/2012 |
| JP | 2016-158911 | 9/2016 |
| JP | 2019-501704 | 1/2019 |
| KR | 10-1859505 | 5/2018 |
| WO | 2007/005018 | 1/2007 |
| WO | 2011/134083 | 11/2011 |
| WO | 2016/114834 | 7/2016 |
| WO | 2020/017854 | 1/2020 |

OTHER PUBLICATIONS

Korean Office Action with English translation for Korean Patent Application or Patent No. 10-2020-0131843, dated Nov. 29, 2021.
Korean Final Office Action with English translation for Korean Patent Application or Patent No. 10-2020-0131843, dated Jun. 15, 2022.
International Search Report, with English translation, corresponding to International Application No. PCT/KR2021/014106 dated Jan. 24, 2022.
Written Opinion, with English translation, corresponding to International Application No. PCT/KR2021/014106, dated Jan. 24, 2022.
Extended European Search Report for European Application No. 21880500.0, dated Feb. 19, 2024.
Japanese Office Action with English translation for Japanese Patent Application No. 2023-522556, dated Apr. 2, 2024.

* cited by examiner

Figure 1:
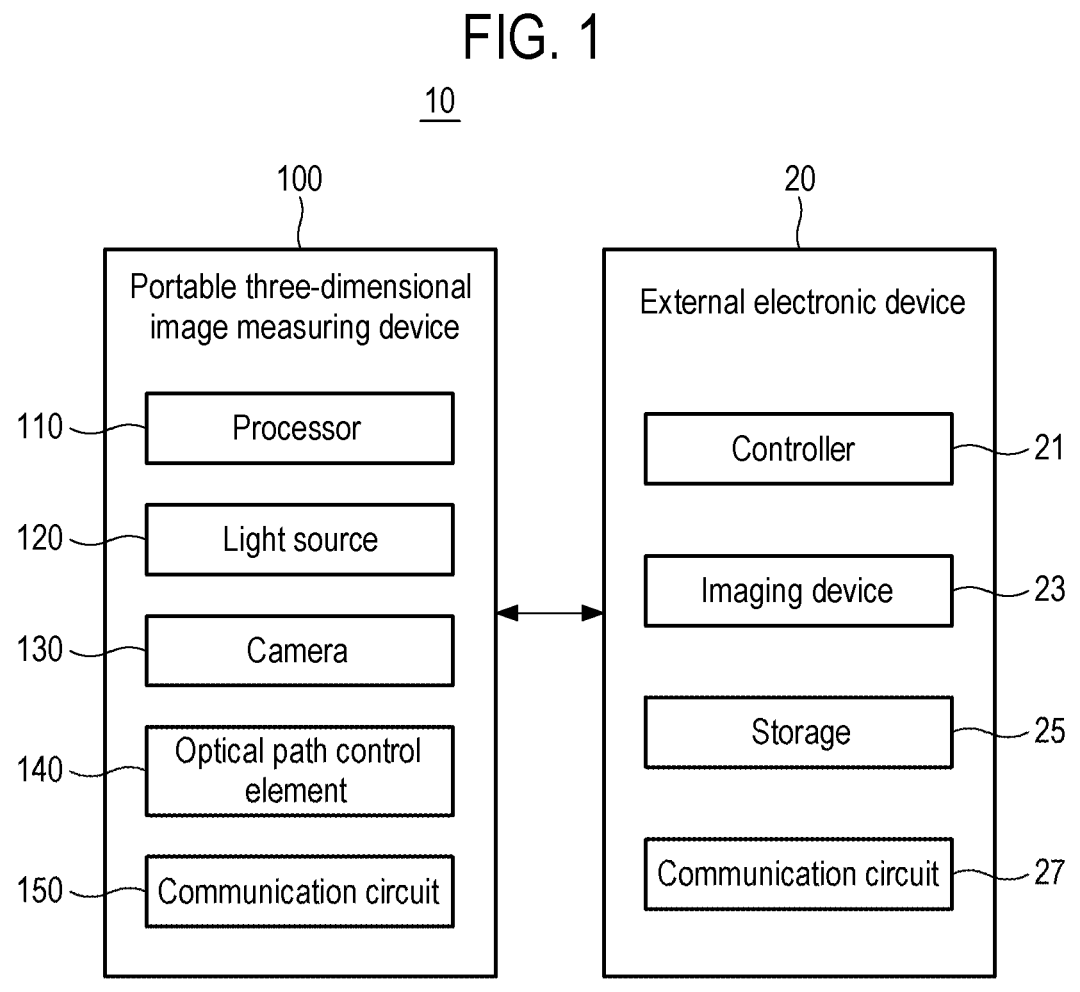

Portable three-dimensional image measuring device

110 Processor

120 Light source

130 Camera

140 Optical path control element

150 Communication circuit

20

External electronic device

21 Controller

23 Imaging device

25 Storage

27 Communication circuit

FIG. 2A

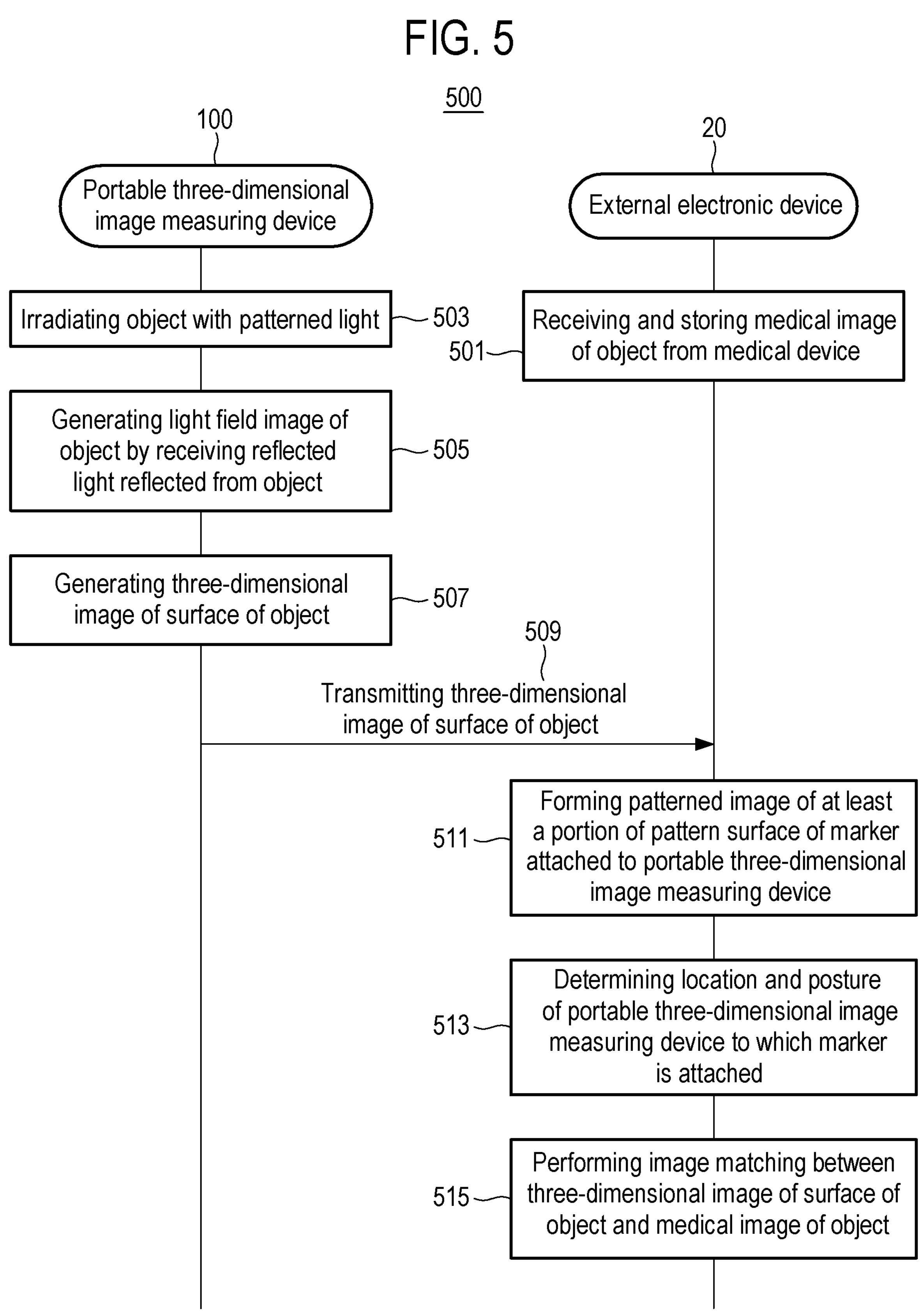
FIG. 5
500
100
Portable three-dimensional image measuring device
20
External electronic device
Irradiating object with patterned light
503
Receiving and storing medical image of object from medical device
501
Generating light field image of object by receiving reflected light reflected from object
505
Generating three-dimensional image of surface of object
507
509
Transmitting three-dimensional image of surface of object
511
Forming patterned image of at least a portion of pattern surface of marker attached to portable three-dimensional image measuring device
513
Determining location and posture of portable three-dimensional image measuring device to which marker is attached
515
Performing image matching between three-dimensional image of surface of object and medical image of object

Figure 6:
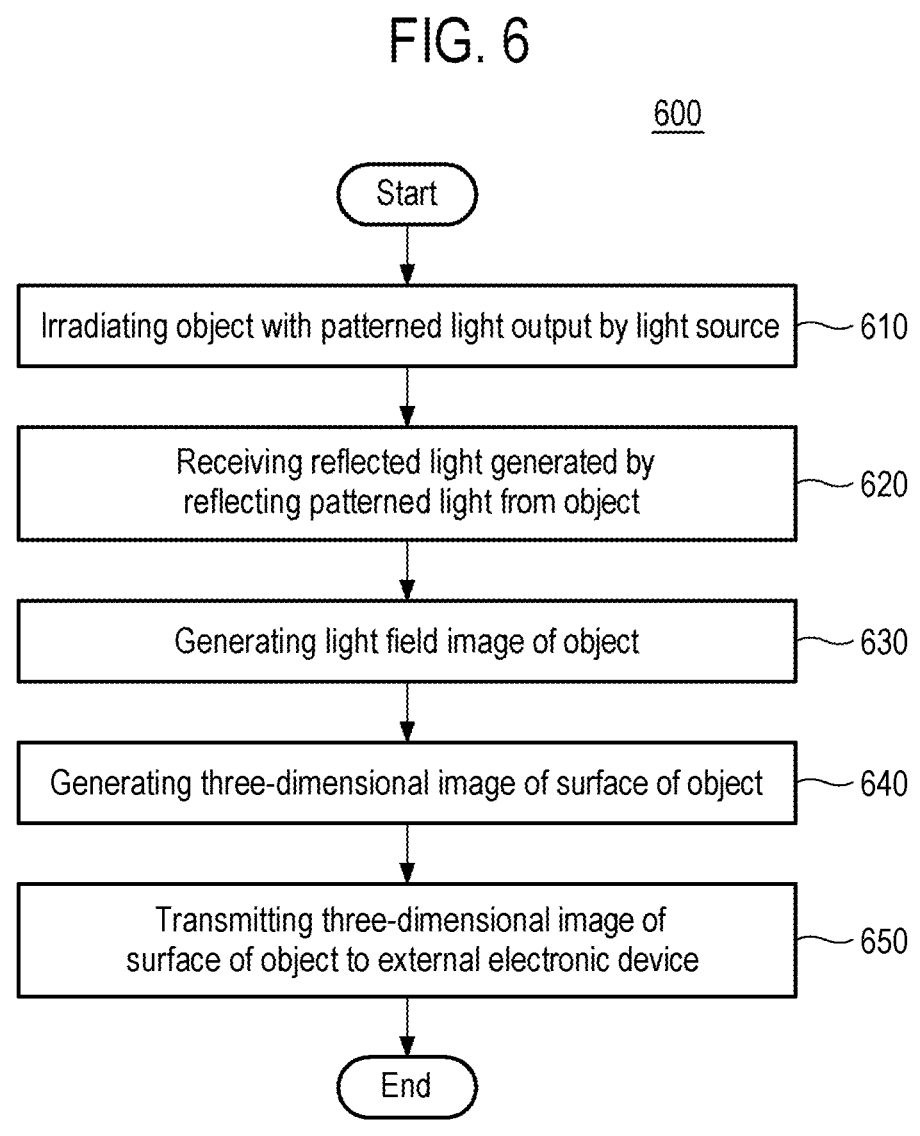

Start

Irradiating object with patterned light output by light source — 610

Receiving reflected light generated by reflecting patterned light from object — 620

Generating light field image of object — 630

Generating three-dimensional image of surface of object — 640

Transmitting three-dimensional image of surface of object to external electronic device — 650

End

PORTABLE THREE-DIMENSIONAL IMAGE MEASURING DEVICE, THREE-DIMENSIONAL IMAGE MEASURING METHOD USING SAME, AND MEDICAL IMAGE MATCHING SYSTEM

CROSS-REFERENCE TO RELATED APPLICATION(S)

This is a continuation application of U.S. patent application Ser. No. 18/248,856 filed Apr. 12, 2023 (now pending), the disclosure of which is incorporated herein by reference in its entirety. U.S. patent application Ser. No. 18/248,856 is a national stage entry of International Application No. PCT/KR2021/014106, filed Oct. 13, 2021, which claims under 35 U.S.C. §§ 119(a) and 365(b) priority to and the benefits of Korean Patent Application No. 10-2020-0131843, filed Oct. 13, 2020, in the Korean Intellectual Property Office, the entire contents of which are incorporated herein by reference.

TECHNICAL FIELD

The present disclosure relates to a portable three-dimensional image measuring device. In particular, the present disclosure relates to a method of performing precise three-dimensional measurement of an object to be measured by providing a portable three-dimensional image measuring device. In addition, the present disclosure relates to a medical image matching system including the portable three-dimensional image measuring device.

This present disclosure is derived from research conducted as part of the WC300 project technology development support. [Project identification number: S2482672, Title of research project: Development of surgical navigation fusion head and neck surgery robot system with matching accuracy of 1 mm or less].

BACKGROUND

Various methods for measuring a three-dimensional image of an object are being used in the industry. Among them, a method of measuring a pattern generated by irradiating an object with certain patterned light, and obtaining a three-dimensional image of the object from the measured pattern is being used. For example, there is a moiré-type three-dimensional image measurement technology that measures a moiré pattern generated by irradiating an object with patterned light and obtains a three-dimensional image of the object from the moiré pattern.

Recently, surgical navigation technology has been used to support doctors in surgical operations. In general, the surgical navigation technology places markers on surgical tools and provides information in the form of displaying the location and posture information of the surgical tool on medical images (e.g., CT images and MRI images) of patients. Since the surgical navigation system needs to acquire and process three-dimensional image information on a specific affected part of a patient, a technique for measuring a three-dimensional image may be utilized.

SUMMARY

In the case of a three-dimensional image measuring device using a stereo camera, a three-dimensional image of an object may be measured through a triangulation method using a fixed pattern. The triangulation method is a method of measuring a three-dimensional image of an object using two or more images captured at different locations. For example, the object may be irradiated with patterned light, images of the object irradiated with the patterned light may be acquired using two or more cameras disposed at different locations, and the three-dimensional image of the object may be acquired using the acquired images. The above three-dimensional image measuring device must include two or more cameras in order to use the triangulation method. The above three-dimensional image measuring device must include a light source that irradiates the object with the patterned light at different locations.

A three-dimensional image measuring device using a chromatic confocal sensor may measure a three-dimensional image of an object by measuring the depth of the object using chromatic aberration of a lens. The three-dimensional image measuring device using a chromatic confocal sensor must perform scanning of the side of the object to acquire the three-dimensional image of the object.

A portable three-dimensional image measuring device according to various embodiments of the present disclosure may include a light source configured to output patterned light, a camera configured to generate a light field image of an object by receiving reflected light generated by reflecting the patterned light from the object, and an optical path control element configured to reflect the patterned light output from the light source so that the object is irradiated with the patterned light, and to transmit the reflected light reflected from the object so that the reflected light reaches the camera. An optical path of the patterned light output from the light source and irradiated onto the object and an optical path of the reflected light reflected from the object and reaching the camera may overlap coaxially in a section between the optical path control element and the object.

A medical image matching system according to various embodiments of the present disclosure may include a portable three-dimensional image measuring device comprising a light source configured to output patterned light, a camera configured to generate a light field image of an object by receiving reflected light generated by reflecting the patterned light from the object, an optical path control element configured to reflect the patterned light output from the light source so that the object is irradiated with the patterned light, and to transmit the reflected light reflected from the object so that the reflected light reaches the camera, a communication circuit, and a processor, an optical path of the patterned light output from the light source and irradiated onto the object and an optical path of the reflected light reflected from the object and reaching the camera may overlap coaxially in a section between the optical path control element and the object, and the processor may be configured to generate a three-dimensional image of the surface of the object using the light field image of the object acquired through the camera and to transmit the three-dimensional image of the surface of the object to an external electronic device through the communication circuit.

A three-dimensional image measuring method of a portable three-dimensional image measuring device according to various embodiments of the present disclosure may include an operation of irradiating an object with patterned light output by a light source through an optical path control element and an operation of generating a light field image of the object by receiving reflected light, which is generated by reflecting the patterned light from the object, by a camera through the optical path control element. An optical path of the patterned light output from the light source and irradiated onto the object and an optical path of the reflected light reflected from the object and reaching the camera may overlap coaxially in a section between the optical path control element and the object.

The three-dimensional image measuring device according to various embodiments of the present disclosure can generate a light field image of an object using one camera that generates a light field image and generate a three-dimensional image of the surface of the object by using the light field image of the object. Since the three-dimensional image measuring device according to various embodiments of the present disclosure can be implemented using only one camera, it can be miniaturized compared to a conventional stereo type three-dimensional image measuring device implemented to include two or more cameras. In addition, since it can be implemented using only one camera, the production cost of the three-dimensional image measuring device can be lowered, and the portability can be enhanced by reducing the weight.

According to various embodiments of the present disclosure, when photographing the object using the miniaturized three-dimensional image measuring device, it is easy for a user to move the three-dimensional image measuring device and to change the photographing posture of the three-dimensional image measuring device. In this case, the user can use the three-dimensional image measuring device to capture various postures (e.g., a lying down posture and a prone posture) of the object.

Since the three-dimensional image measuring device according to various embodiments of the present disclosure can use the camera that generates the light field image, the three-dimensional image of the object can be generated even with a single measurement.

In the three-dimensional image measuring device according to various embodiments of the present disclosure, since the optical axis of a light source emitting patterned light and the optical axis of a camera receiving light reflected from an object are coaxial in a partial section, distortion of an acquired light field image of the object can be minimized, and the device can be miniaturized. When the optical axis of the light source and the optical axis of the camera are coaxial in the partial section, the distortion of the light field image due to an inclination of the patterned light emitted from the light source may not occur.

In the three-dimensional image measuring device according to various embodiments of the present disclosure, since the optical axis of the light source emitting the patterned light and the optical axis of the camera receiving the light reflected from the object are coaxial in the partial section, the object can be uniformly irradiated with the patterned light, so that the loss of the amount of light can be minimized.

BRIEF DESCRIPTION OF DRAWINGS

FIG. 1 is a block diagram showing a medical image matching system according to various embodiments of the present disclosure.

Figure 2A:
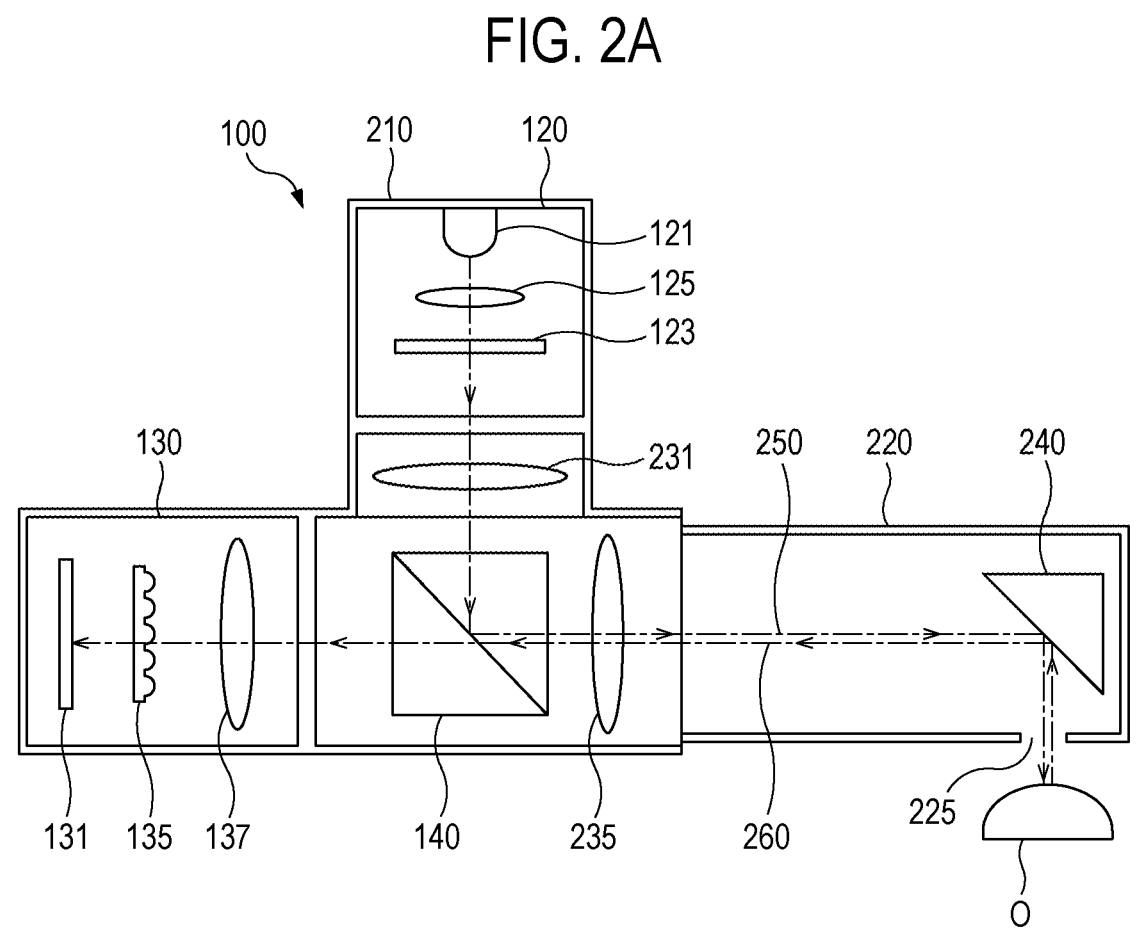

FIGS. 2A and 2B are cross-sectional views of a portable three-dimensional image measuring device according to various embodiments.

FIG. 5 is an operation flowchart of the medical image matching system according to various embodiments of the present disclosure.

FIG. 6 is an operation flowchart of the portable three-dimensional image measuring device according to various embodiments of the present disclosure.

FIG. 7 is a view showing an example in which the medical image matching system according to various embodiments of the present disclosure is used.

FIG. 11 is a view for explaining the light field image including the plurality of sub-images having different subject depths according to various embodiments of the present disclosure.

DETAILED DESCRIPTION

Figure 2B:
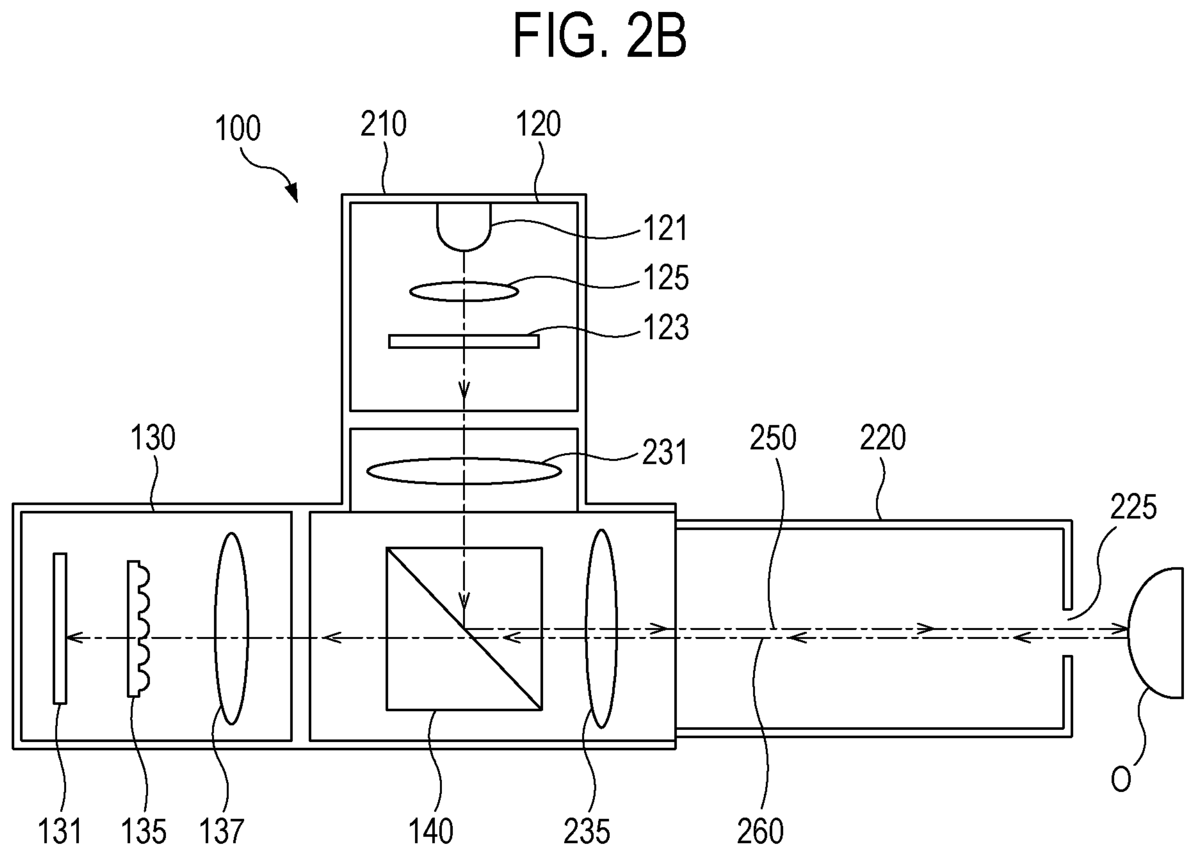

Embodiments of the present disclosure are illustrated for describing the technical spirit of the present disclosure. The scope of the claims according to the present disclosure is not limited to the embodiments described below or to the detailed descriptions of these embodiments.

All technical or scientific terms used herein have meanings that are generally understood by a person having ordinary knowledge in the art to which the present disclosure pertains, unless otherwise specified. The terms used herein are selected for only more clear illustration of the present disclosure, and are not intended to limit the scope of claims in accordance with the present disclosure.

The expressions "include," "provided with," "have" and the like used herein should be understood as open-ended terms connoting the possibility of inclusion of other embodiments, unless otherwise mentioned in a phrase or sentence including the expressions.

A singular expression can include meanings of plurality, unless otherwise mentioned, and the same is applied to a singular expression recited in the claims.

The terms "first," "second," etc. used herein are used to identify a plurality of components from one another, and are not intended to limit the order or importance of the relevant components.

The term "unit" used in these embodiments means a software component or hardware component, such as a field-programmable gate array (FPGA) and an application specific integrated circuit (ASIC). However, a "unit" is not limited to software and hardware, it may be configured to be an addressable storage medium or may be configured to run on one or more processors 110. For example, a "unit" may include components, such as software components, object-oriented software components, class components, and task components, as well as processors 110, functions, attributes, procedures, subroutines, segments of program codes, drivers, firmware, micro-codes, circuits, data, databases, data structures, tables, arrays, and variables. Functions provided in components and "unit" may be combined into a smaller number of components and "units" or further subdivided into additional components and "units."

The expression "based on" used herein is used to describe one or more factors that influence a decision, an action of judgment or an operation described in a phrase or sentence including the relevant expression, and this expression does not exclude additional factor influencing the decision, the action of judgment or the operation.

When a certain component is described as being "coupled to" or "connected to" another component, this should be understood as meaning that the certain component may be coupled or connected directly to the other component or that the certain component may be coupled or connected to the other component via a new intervening component.

Hereinafter, embodiments of the present disclosure will be described with reference to the accompanying drawings. In the accompanying drawings, like or relevant components are indicated by like reference numerals. In the following description of embodiments, repeated descriptions of the identical or relevant components will be omitted. However, even if a description of a component is omitted, such a component is not intended to be excluded in an embodiment.

Although process steps, method steps, algorithms, etc. are described in a sequential order in the shown flowcharts, such processes, methods, and algorithms may be configured to operate in any suitable order. In other words, the steps of the processes, methods, and algorithms described in various embodiments of the present disclosure do not have to be performed in the order described in the present disclosure. In addition, although some steps are described as being performed asynchronously, they may be performed concurrently in other embodiments. Further, illustration of processes by depiction in the drawings does not mean that the illustrated processes are exclusive of other changes and modifications thereto, that any of the illustrated processes or steps thereof are essential to one or more of various embodiments of the present disclosure, and that the illustrated processes are preferable.

FIG. 1 is a block diagram showing a medical image matching system 10 according to various embodiments of the present disclosure.

Referring to FIG. 1, the medical image matching system 10 according to various embodiments may include a portable three-dimensional image measuring device 100 and an external electronic device 20. The portable three-dimensional image measuring device 100 and the external electronic device 20 may communicate with each other to transmit/receive various data (e.g., images). Even if some of the components shown in FIG. 1 are omitted or replaced, there will be no problem in implementing various embodiments disclosed in the present disclosure.

The portable three-dimensional image measuring device 100 according to various embodiments may include a processor 110, a light source 120, a camera 130, an optical path control element 140, and a communication circuit 150. The portable three-dimensional image measuring device 100 may further include a first housing (not shown) and a second housing (not shown).

The processor 110 according to various embodiments may be a component capable of performing calculations or data processing related to control and/or communication of other components of the portable three-dimensional image measuring device 100. The processor 110 may be operatively connected to other components of the portable three-dimensional image measuring device 100, for example. The processor 110 may load commands or data received from other components of the portable three-dimensional image measuring device 100 into a memory (not shown), process the commands or data stored in the memory, and output the resulting data.

The light source 120 according to various embodiments may output patterned light. The light source 120 may irradiate an object with the patterned light. The patterned light may be light having a specific pattern or light having a pattern with a constant or specific period in order to measure a three-dimensional image of the object. The patterned light may include, for example, patterned light in the form of random dots, patterned light in the form of a checkered pattern, patterned light in which the brightness of stripes is in the form of a sine wave, patterned light in the form of on-off with repeated bright and dark portions, and triangular wave patterned light in which a change in brightness is a triangular waveform. However, this is only for the purpose of explanation, and the shape of the patterned light is not limited thereto.

The light source 120 according to various embodiments may include a pattern unit in which a plurality of patterns are formed, and an LED that irradiates the pattern unit with light. The light source 120 may further include a condensing lens configured to condense the light output from the LED and irradiate the pattern unit with the condensed light. The light output from the LED may reflect the patterns by passing through the pattern unit in which the plurality of patterns are formed. The LED may emit infrared light, for example, but is not limited thereto.

The camera 130 according to various embodiments may be a component that captures an image of an object. The camera 130 may acquire image data of the object by photographing the object, and may acquire a three-dimensional image of the object by processing the acquired image data. For example, the camera 130 may acquire the image of the object by photographing the object irradiated with the patterned light. The processor 110 may generate the three-dimensional image of the object based on a phase shift method using the patterned light. For example, when an object is irradiated with the patterned light of a certain shape through the light source 120, the intensity of light appearing on the surface of the object may vary according to the curvature of the surface of the object. In this case, the camera 130 may generate a light field image of the object reflected with the pattern, and the processor 110 may generate a three-dimensional image for the surface of the object by generating phase data from the light field image and calculating the height of each point constituting the surface of the object.

The camera 130 according to various embodiments may be a light field camera 130 that generates a light field image. The light field camera 130 may be configured to determine the depth of the object posteriorly after photographing the object, and to combine images having different depths of the object. An image sensor of the light field camera 130 may have a posterior and variable object depth.

The camera 130 according to various embodiments may include a condensing lens, a lens array, and an image sensor. The condensing lens may, for example, condense light entering from an object. The lens array may be, for example, a lens in which a plurality of micro lenses are arranged. The image sensor may, for example, capture light passing through the lens array and generate a light field image using the captured light. The image sensor may be divided into regions corresponding to the respective ones of the plurality of micro lenses. The image sensor may include, for example, a charge-coupled device (CCD) sensor or a complementary metal-oxide semiconductor (CMOS) sensor. A detailed description of each component included in the camera 130 will be described in FIGS. 8 to 11.

The light field image generated by the camera 130 according to various embodiments may include a plurality of sub-images that store color information and direction information of light together. For example, when an object is irradiated with patterned light and reflected light reflected from the object is received by the camera 130, the light field image may be an image in which a plurality of sub-images including color information and direction information of the reflected light are combined. The camera 130 may perform a refocusing process using the plurality of sub-images included in the light field image. For example, in the refocusing process, the camera 130 may generate an image of a desired depth by combining the depth of a desired object and color information of pixels corresponding to the optical path and direction backward calculated accordingly, among pixels of the light field image. For example, the camera 130 may generate an image in which all regions of the object are in focus during the refocusing process. In order for the camera 130 to form an image of an accurate photographing target region, a distance between the portable three-dimensional image measuring device 100 and the photographing target region of the object needs to be appropriately adjusted. When using the camera 130 that generates the light field image, since the depth of the object can be determined posteriorly and a focused light field image can be generated for all regions of the object, there is no need to adjust the focal length in advance. In the case of the camera 130 generating the light field image, a measurable depth range is wider than that of the camera 130 using a general lens, so that a three-dimensional image of the object can be acquired with one shot.

The optical path control element 140 according to various embodiments may reflect the patterned light in a specific direction so that the object is irradiated with the patterned light output from the light source 120. The optical path control element 140 may transmit the reflected light reflected from the object to reach the camera 130. The optical path control element 140 may be, for example, a transflective mirror. According to various embodiments, the light source 120 and the camera 130 may be disposed perpendicular to each other with respect to the optical path control element 140.

The light source 120, the camera 130, and the optical path control element 140 may be disposed inside the first housing according to various embodiments. The second housing according to various embodiments may be coupled to the first housing and may have an opening through which the object is irradiated with the patterned light output from the light source 120. The second housing may be rotatably coupled to the first housing. The first housing or the second housing may be coupled with a component (e.g., a handle) that facilitates a user's movement, carrying, and use of the portable three-dimensional image measuring device 100.

According to various embodiments, the communication circuit 150 may establish a communication channel with the external electronic device 20 and transmit/receive various data to/from the external electronic device 20. According to various embodiments, the communication circuit 150 may include a cellular communication module and be configured to be connected to a cellular network (e.g., 3G, LTE, 5G, Wibro, or Wimax). According to various embodiments, the communication circuit 150 may include a short-range communication module to transmit/receive data to/from the external electronic device 20 by using short-range communication (e.g., Wi-Fi, Bluetooth, Bluetooth Low Energy (BLE), or UWB), but it is not limited thereto.

The processor 110 according to various embodiments may generate a three-dimensional image of the surface of the object using the light field image of the object acquired through the camera 130. For example, the light intensity of the emitted patterned light displayed on the surface of the target region to be actually photographed may vary according to the curvature of the surface of the target region of the object to be photographed. The processor 110 may use the light field image of the object to measure the intensity of light that varies according to the curvature of the surface of the object, generate phase data from the measured light intensity, and calculate the height of each point constituting the surface. The processor 110 may generate a three-dimensional image of the surface of the object by calculating the height of each point constituting the surface of the object.

The processor 110 according to various embodiments may transmit the three-dimensional image of the surface of the object to the external electronic device 20 through the communication circuit 150.

The external electronic device 20 according to various embodiments may include a controller 21, an imaging device 23, a storage 25, and a communication circuit 27. The controller 21 according to various embodiments may be a component capable of performing calculations or data processing related to control and/or communication of other components of the external electronic device 20. The controller 21 may be operatively connected to other components of the external electronic device 20, for example.

The imaging device 23 according to various embodiments may image at least a portion of a pattern surface of a marker (not shown) attached to the portable three-dimensional image measuring device 100 to form a pattern image of the at least a portion of the pattern surface. The imaging device 23 may include, for example, at least two or more cameras capable of forming an image of at least a portion of the marker. The external electronic device 20 may determine the location and/or posture of the marker or the portable three-dimensional image measuring device 100 to which the marker is attached, using the formed pattern image.

For example, when the pattern image of the marker is acquired, the external electronic device 20 may extract at least one among sub-patterns, from the pattern image as a basic unit constituting the marker pattern. The location of at least one extracted sub-pattern within the entire pattern may be determined, and the posture of the marker may be determined based on the determined location of the sub-pattern within the entire pattern. Here, the posture of the marker may mean a three-dimensional direction or orientation of the marker relative to the imaging device 23. For example, the location of the marker or the portable three-dimensional image measuring device 100 may be determined using triangulation based on two images having a stereoscopic relationship among images formed by the imaging device 23 including at least two cameras. When the location and posture of the marker are determined as described above, the location and posture of the portable three-dimensional image measuring device 100 to which the marker is attached may be determined based on the geometric relationship between the marker and the portable three-dimensional image measuring device 100 to which the marker is attached.

The storage 25 according to various embodiments may store various data used by at least one component (e.g., the controller 21) of the external electronic device 20. For example, the controller 21 may cause the storage 25 to store the three-dimensional image of the surface of the object received from the portable three-dimensional image measuring device 100. For example, the controller 21 may cause the storage 25 to store medical images (e.g., CT images and MRI images) received from a medical device (not shown).

The communication circuit 27 of the external electronic device 20 according to various embodiments may establish a communication channel with the portable three-dimensional image measuring device 100 and transmit/receive various data to/from the portable three-dimensional image measuring device 100. According to various embodiments, the communication circuit 27 of the external electronic device 20 may include a cellular communication module and be configured to be connected to a cellular network (e.g., 3G, LTE, 5G, Wibro, or Wimax). According to various embodiments, the communication circuit 27 of the external electronic device 20 includes a short-range communication module to transmit/receive data to/from the portable three-dimensional image measuring device 100 by using short-range communication (e.g., Wi-Fi, Bluetooth, Bluetooth Low Energy (BLE), or UWB), but it is not limited thereto.

The controller 21 of the external electronic device 20 according to various embodiments may perform image matching between the three-dimensional image of the surface of the object received from the portable three-dimensional image measuring device 100 and the medical image of the object. The three-dimensional image of the surface of the object generated by the portable three- dimensional image measuring device 100 may be the external surface of a target included in the medical image or a portion thereof. For example, if the medical image is an image modeling the three-dimensional shape of a head of the object, the three-dimensional image of the surface of the object may be an image obtained by measuring the external shapes of the eyes, nose, mouth, cars, etc. on the surface of the object's head.

According to various embodiments, the three-dimensional image of the surface of the object may have a unique coordinate system (for example, x1y1z1 coordinate system) of the portable three-dimensional image measuring device 100. The coordinate system of the three-dimensional image of the surface of the object may be different from the coordinate system of the medical image (for example, x2y2z2 system) and the coordinate system of the external electronic device 20 (for example, x0y0z0 system). The coordinate system of the external electronic device 20 may mean, for example, the coordinate system of the imaging device of the external electronic device 20. A detailed image matching method will be described with reference to FIG. 4 later.

FIGS. 2A and 2B are cross-sectional views of the portable three-dimensional image measuring device 100 according to various embodiments. Specifically, FIGS. 2A and 2B are views schematically showing only some of the components of the portable three-dimensional image measuring device 100 in order to explain the arrangement relationship between the components. Contents overlapping with those described in FIG. 1 will be omitted.

Referring to FIG. 2A, the portable three-dimensional image measuring device 100 according to various embodiments may include the light source 120, the camera 130, and the optical path control element 140. The portable three-dimensional image measuring device 100 may include a first housing 210 in which the light source 120, the camera 130, and the optical path control element 140 are disposed, and a second housing 220 that is coupled to the first housing 210 and is formed with an opening 225 through which an object O is irradiated with the patterned light output from the light source 120. The light source 120 and the camera 130 according to various embodiments may be disposed perpendicular to each other with respect to the optical path control element 140. According to various embodiments, at least one condensing lens 231 or 235 for condensing light may be disposed around the optical path control element 140.

The light source 120 according to various embodiments may include a pattern unit 123 in which a plurality of patterns are formed, and an LED 121 that irradiates the pattern unit 123 with light. The light source 120 may further include a condensing lens 125, which is configured to condense the light output from the LED 121 and irradiate the pattern unit 123 with the condensed light, between the pattern unit 123 and the LED 121. The light output from the LED 121 may reflect the patterns by passing through the pattern unit 123. According to various embodiments, the patterned light output from the light source 120 may be incident to the optical path control element 140. The patterned light incident to the optical path control element 140 may be reflected toward the second housing 220 so that the object O can be irradiated with the patterned light. The patterned light incident into the second housing 220 may be reflected by a reflective mirror 240 so that the object O can be irradiated with the patterned light through the opening 225 of the second housing 220.

According to various embodiments, the patterned light with which the object O is irradiated may be reflected by the object O. The reflected light reflected from the object O may be incident again into the second housing 220 through the opening 225. The reflected light may be reflected by the reflective mirror 240 and incident to the optical path control element 140. The reflected light incident to the optical path control element 140 may pass through the optical path control element 140 and reach the camera 130. The reflected light passing through the optical path control element 140 may pass through a condensing lens 137 and pass through a lens array 135 in which a plurality of micro lenses are arranged. An image sensor 131 may capture the reflected light passing through the lens array 135. The image sensor 131 may generate a light field image of the object O by capturing the reflected light. The light field image of the object O may be an image of patterned light with which the object O is irradiated. The processor 110 may generate a three-dimensional image of the surface of the object O by using the light field image of the object O, and may transmit the three-dimensional image of the surface of the object O to the external electronic device 20 through the communication circuit 150.

According to various embodiments, an optical path 250 of the patterned light which is output from the light source 120 and irradiated onto the object O and an optical path 260 of the reflected light which is reflected from the object O and reaches the camera 130 may overlap in a coaxial manner in a section between the optical path control element 140 and the object O. When the optical path 250 of the patterned light with which the object O is irradiated and the optical path 260 of the reflected light reflected from the object O are coaxial, the portable three-dimensional image measuring device 100 can be miniaturized and an accurate image of the object O may be acquired. For example, if the optical path 250 of the patterned light with which the object O is irradiated and the optical path 260 of the reflected light reflected from the object O are not coaxial, the patterned light may obliquely irradiate the object O or the reflected light reflected from the object O may obliquely reach the camera 130. A pattern formed on the object O by the patterned light irradiate obliquely may have a distorted shape compared to a pattern formed on the object O by the patterned light irradiate perpendicularly. In this case, a distorted image of the object O may be acquired. On the other hand, when the optical path 250 of the patterned light with which the object O is irradiated and the optical path 260 of the reflected light reflected from the object O are coaxial, a user may use the three-dimensional image measuring device 100 to acquire an accurate and undistorted image of the object O.

According to various embodiments, when the optical path 250 of the patterned light with which the object O is irradiated and the optical path 260 of the reflected light reflected from the object O are coaxial, the portable three-dimensional image measuring device 100 may easily photograph the object O. When photographing the object O using the miniaturized three-dimensional image measuring device 100, the user can easily move the three-dimensional image measuring device 100 and easily change the photographing posture of the three-dimensional image measuring device 100. In the above case, the user may use the three-dimensional image measuring device 100 to capture various postures (e.g., a lying down posture and a prone posture) of the object.

According to various embodiments, when the optical path 250 of the patterned light with which the object O is irradiated and the optical path 260 of the reflected light reflected from the object O are coaxial, the portable three-dimensional image measuring device 100 may acquire the image of the object using one camera 130 instead of acquiring the image of the object through the triangulation method using two or more cameras. Therefore, the portable three-dimensional image measuring device 100 can be miniaturized compared to the conventional stereo-type 3D image measuring device implemented by including two or more cameras, which may result in reduction of production cost and enhanced portability by reducing weight.

In the three-dimensional image measuring device 100 according to various embodiments, since the optical path 250 of the patterned light with which the object O is irradiated and the optical path 260 of the reflected light reflected from the object O are coaxial, the object O may be uniformly irradiated with the patterned light, and loss of light quantity may be minimized.

Referring to FIG. 2B, the portable three-dimensional image measuring device 100 according to various embodiments may not include the separate reflective mirror 240 shown in FIG. 2A. In this case, the object O may be irradiated with the patterned light reflected from the optical path control element 140 through the opening 225 formed on the optical path 250 of the patterned light without additional reflection. In addition to the structure shown in FIGS. 2A and 2B, a variety of structures in which the optical path 250 of the patterned light with which the object O is irradiated and the optical path 260 of reflected light reflected from the object O are coaxial may be applied to the portable three-dimensional image measuring device 100.

Figure 3:
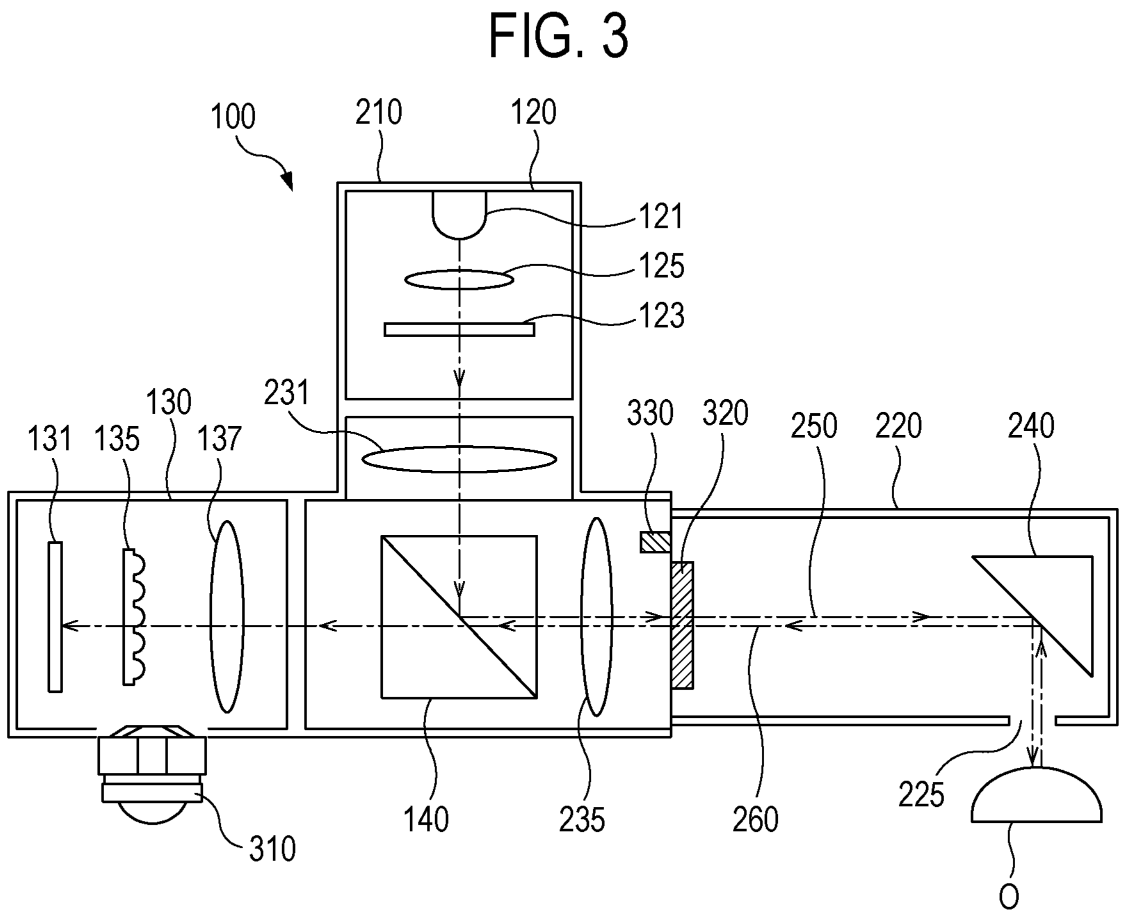
FIG. 3 is a cross-sectional view of a portable three-dimensional image measuring device according to various embodiments.

FIG. 3 is a cross-sectional view of the portable three-dimensional image measuring device 100 according to various embodiments. Specifically, FIG. 3 is a view schematically showing only some of the components of the portable three-dimensional image measuring device 100 in order to explain the arrangement relationship between the components. Contents overlapping with those described in FIG. 2 are omitted.

The portable three-dimensional image measuring device 100 according to various embodiments may further include a marker 310. For example, the marker 310 may be attached to the first housing 210 of the portable three-dimensional image measuring device 100. The marker 310 may include a pattern surface on which a pattern is formed and a lens configured to identify at least a portion of the pattern uniquely appearing from the outside of the marker 310 according to a direction viewed from the outside of the marker 310. The lens of the marker 310 may be a ball lens, and the pattern surface may have a curved shape.

The external electronic device 20 according to various embodiments may image at least a portion of the pattern surface of the marker 310 through the imaging device 23 to form a pattern image for at least a portion of the pattern surface. The external electronic device 20 may determine the location or coordinate and posture or orientation of the portable three-dimensional image measuring device 100 to which the marker 310 is attached, based on the formed pattern image.

The location of the portable three-dimensional image measuring device 100 may be defined by spatial coordinates such as coordinates on the x, y, and z axes of the Cartesian coordinate system. The posture of the portable three-dimensional image measuring device 100 may be defined as roll, pitch, and yaw. The external electronic device 20 may capture an image of the marker 310 attached to the portable three-dimensional image measuring device 100 through the imaging device 23, thereby tracking the location and posture of the portable three-dimensional image measuring device 100.

For example, the external electronic device 20 may form an image of at least a portion of the pattern surface of the marker 310 attached to the portable three-dimensional image measuring device 100 through the imaging device 23. For example, the imaging device 23 of the external electronic device 20 may form a pattern image of at least a portion of a pattern visually identified from the outside of the marker 310 through a ball lens of the marker 310. When the pattern image of at least a portion of the pattern surface is acquired, the external electronic device 20 may process information extracted from the pattern image of at least the portion of the pattern surface to determine the location and posture of the marker 310. The external electronic device 20 may determine the location and posture of the portable three-dimensional image measuring device 100 to which the marker 310 is attached, based on the location and posture of the marker 310. A specific method of calculating the location and posture of the marker 310 using the image of at least the portion of the pattern surface may be the same as a general optical tracking method.

The marker 310 according to various embodiments may be installed to be movable from a predetermined location of the portable three-dimensional image measuring device 100. The processor 110 may transmit information, which indicates the displacement of the marker 310 from the predetermined location of the portable three-dimensional image measuring device 100, to the external electronic device 20 through the communication circuit 150. The external electronic device 20 receives the information indicating the displacement of the marker 310 and may correct the location or posture of the portable three-dimensional image measuring device 100 based on the received information indicating the displacement of the marker 310. Information on the corrected location or posture of the portable three-dimensional image measuring device 100 may be used for image matching between the three-dimensional image of the surface of the object O and a medical image.

The three-dimensional image of the surface of the object O may have a unique coordinate system (for example, x1y1z1 coordinate system) of the portable three-dimensional image measuring device 100. The coordinate system of the three-dimensional image of the surface of the object O may be different from the coordinate system (for example, x2y2z2) of the medical image and may be different from the coordinate system (for example, x0y0z0) of the external electronic device 20.

The medical image matching system 10 according to various embodiments may transform or align the coordinate system (for example, x2y2z2) of the medical image and the coordinate system (for example, x1y1z1) of the three-dimensional image of the surface of the object O into the coordinate system (for example, x0y0z0) of the external electronic device 20. The external electronic device 20 may perform matching between the medical image and the three-dimensional image of the surface of the object O, which have different coordinate systems. In order to match between the medical image and the three-dimensional image of the surface of the object O, the external electronic device 20 may extract a surface image from the medical image and perform matching between the extracted surface image and the received three-dimensional image of the surface of the object O. Here, the surface image extracted from the medical image may have the same coordinate system (for example, x2y2z2) of the medical image. In addition, the external electronic device 20 may transform the coordinate system (for example, x1y1z1) of the three-dimensional image of the surface of the object O into the coordinate system (for example, x0y0z0) of the external electronic device 20 by mediation of the marker 310 attached to the portable three-dimensional image measuring device 100. In addition, the medical image and the surface image extracted from the medical image may be transformed into the coordinate system (for example, x0y0z0) of the external electronic device 20. The external electronic device 20 may perform matching between the three-dimensional image of the surface of the object O and the medical image using various image matching algorithms. For example, the external electronic device 20 may perform matching using an interactive closest point (ICP) algorithm.

The portable three-dimensional image measuring device 100 according to various embodiments may further include a bearing 320 and a sensor 330. The second housing 220 according to various embodiments may be rotatably coupled to the first housing 210. The bearing 320 may be a mechanical element that rotatably couples the second housing 220 to the first housing 210. The second housing 220 may rotate based on the central axis of the bearing 320 and may rotate independently of the first housing 210. The sensor 330 may be a sensor that senses an angle at which the second housing 220 rotates with respect to the first housing 210. The sensor 330 may be, for example, a gyro sensor or an encoder. The processor 110 according to various embodiments may transmit information on the angle at which the second housing 220 rotates with respect to the first housing 210, to the external electronic device 20 through the communication circuit 150.

Figure 4:
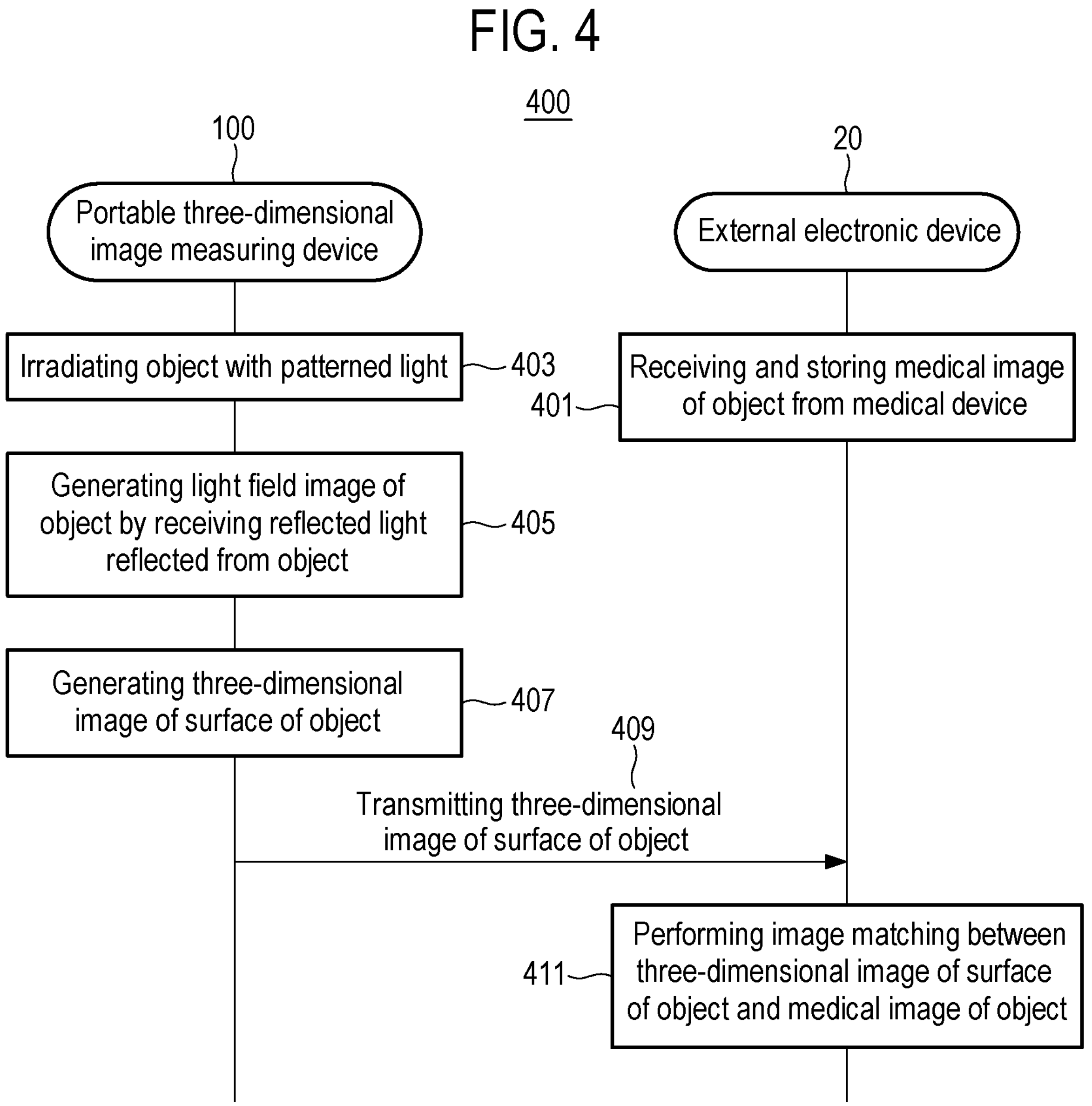
FIG. 4 is an operation flowchart of the medical image matching system according to various embodiments of the present disclosure.

FIG. 4 is an operation flowchart of the medical image matching system 10 according to various embodiments of the present disclosure.

Referring to the operation flowchart 400, in operation 401, the external electronic device 20 according to various embodiments may receive and store a medical image of an object from a medical device. The medical image may be, for example, a CT image or an MRI image.

In operation 403, the portable three-dimensional image measuring device 100 according to various embodiments may irradiate the object with patterned light. For example, the portable three-dimensional image measuring device 100 may output patterned light through the light source 120. The patterned light output through the light source 120 may be reflected by the optical path control element 140 and the object may irradiated with the patterned light.

In operation 405, the portable three-dimensional image measuring device 100 according to various embodiments may generate a light field image of the object by receiving reflected light reflected from the object. For example, the reflected light reflected from the object may reach the camera 130 through the optical path control element 140. The camera 130 may generate the light field image of the object by receiving the reflected light.

In operation 407, the portable three-dimensional image measuring device 100 according to various embodiments may generate a three-dimensional image of the surface of the object by using the light field image of the object. For example, the processor 110 may measure the light intensity of patterned light included in the light field image of the object and generate phase data based on the measured light intensity of the patterned light. The processor 110 may generate the three-dimensional image of the surface of the object by calculating the height of each point constituting the surface of the object based on the generated phase data.

In operation 409, the portable three-dimensional image measuring device 100 according to various embodiments may transmit the three-dimensional image of the surface of the object to the external electronic device 20. For example, the processor 110 of the portable three-dimensional image measuring device 100 may transmit the three-dimensional image of the surface of the object to the external electronic device 20 through the communication circuit 150.

In operation 411, the external electronic device 20 according to various embodiments may perform image matching between the three-dimensional image of the surface of the object received from the portable three-dimensional measurement device and a pre-stored medical image of the object.

FIG. 5 is an operation flowchart of the medical image matching system according to various embodiments of the present disclosure. Contents overlapping with those described in FIG. 4 are omitted.

Referring to the operation flowchart 500, in operation 501, the external electronic device 20 according to various embodiments may receive and store a medical image of an object from a medical device.

In operation 503, the portable three-dimensional image measuring device 100 according to various embodiments may irradiate the object with patterned light.

In operation 505, the portable three-dimensional image measuring device 100 according to various embodiments may generate a light field image of the object by receiving reflected light reflected from the object.

In operation 507, the portable three-dimensional image measuring device 100 according to various embodiments may generate a three-dimensional image of the surface of the object by using the light field image of the object.

In operation 509, the portable three-dimensional image measuring device 100 according to various embodiments may transmit the three-dimensional image of the surface of the object to the external electronic device 20.

In operation 511, the external electronic device 20 according to various embodiments may form an image of at least a portion of the pattern surface of the marker 310 attached to the portable three-dimensional image measuring device 100. For example, the external electronic device 20 may form a pattern image of at least the portion of the pattern surface of the marker 310 through an imaging device.

In operation 513, the external electronic device 20 according to various embodiments may determine the location and posture of the portable three-dimensional image measuring device 100 to which the marker 310 is attached, based on the formed pattern image. For example, the external electronic device 20 may process information extracted from the pattern image of at least the portion of the pattern surface to determine the location and posture of the marker 310. The external electronic device 20 may determine the location and posture of the portable three-dimensional image measuring device 100 to which the marker 310 is attached, based on the location and posture of the marker 310.

In operation 515, the external electronic device 20 according to various embodiments may perform image matching between the three-dimensional image of the surface of the object and a medical image of the object. For example, the external electronic device 20 may transform the coordinate system of the three-dimensional image of the surface of the object into the coordinate system of the external electronic device 20 by mediation of the marker 310 attached to the portable three-dimensional image measuring device 100. The external electronic device 20 may transform the coordinate system of the medical image into the coordinate system of the external electronic device 20. After completing the coordinate system transformation, the external electronic device 20 may perform image matching between the three-dimensional image of the surface of the object and the medical image of the object.

FIG. 6 is an operation flowchart of the portable three-dimensional image measuring device 100 according to various embodiments of the present disclosure.

Referring to the operation flowchart 600, in operation 610, the portable three-dimensional image measuring device 100 according to various embodiments may irradiate an object with patterned light output by the light source 120. For example, the portable three-dimensional image measuring device 100 may output the patterned light through the light source 120. The output patterned light may be reflected by the optical path control element 140 and the object may be irradiated with the reflected patterned light.

In operation 620, the portable three-dimensional image measuring device 100 according to various embodiments may receive reflected light generated by reflecting the patterned light from the object. For example, the patterned light with which the object is irradiated may be reflected by the object and incident again into the portable three-dimensional image measuring device 100. The reflected light may pass through the optical path control element 140 and reach the camera 130.

In operation 630, the portable three-dimensional image measuring device 100 according to various embodiments may generate a light field image of the object by receiving the reflected light through the camera 130. In operation 640, the portable three-dimensional image measuring device 100 according to various embodiments may generate a three-dimensional image of the surface of the object based on the light field image of the object. In operation 650, the portable three-dimensional image measuring device 100 according to various embodiments may transmit the three-dimensional image of the surface of the object to the external electronic device.

Figure 7:
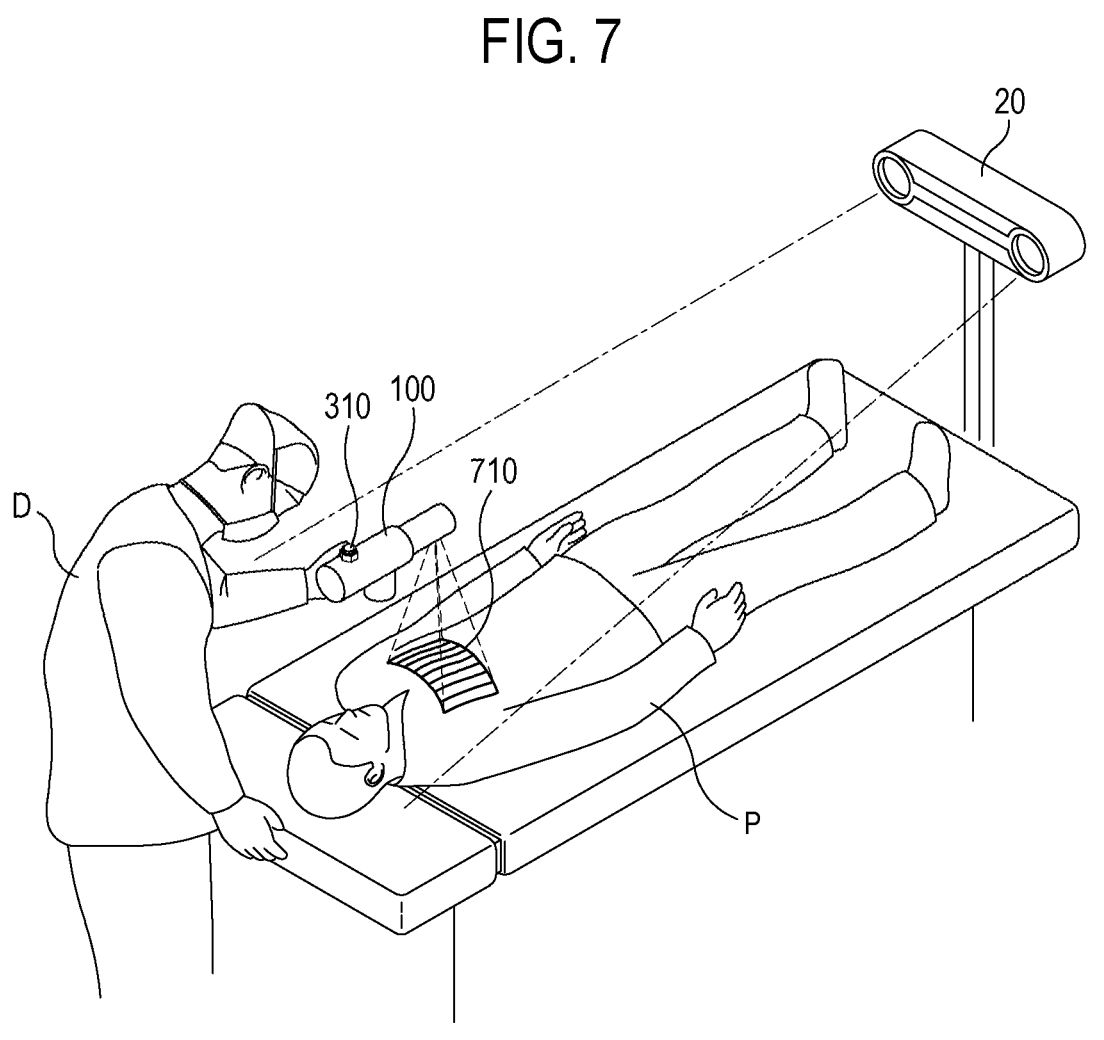

FIG. 7 is a view showing an example in which the medical image matching system 10 according to various embodiments of the present disclosure is used.

Referring to FIG. 7, a doctor (D) may acquire a three-dimensional image of a surface of a patient (P) using the portable three-dimensional image measuring device 100. For example, the doctor D may use the portable three-dimensional image measuring device 100 to irradiate the surface of the patient P with patterned light. A pattern 710 may be formed on the surface of the patient P by the patterned light with which the surface of the patient P is irradiated. The portable three-dimensional image measuring device 100 may generate a light field image of the patient P by receiving reflected light reflected from the patient P. The light field image of the patient P may be, for example, an image in which a plurality of sub-images of the irradiated pattern 710 are combined. The portable three-dimensional image measuring device 100 may generate the three-dimensional image of the surface of the patient P using the light field image of the patient P. The portable three-dimensional image measuring device 100 may transmit the generated three-dimensional image of the surface of the patient P to the external electronic device 20.

The external electronic device 20 according to various embodiments may capture an image of at least a portion of the pattern surface of the marker 310 attached to the portable three-dimensional image measuring device 100 through an imaging device to form a pattern image of the at least a portion of the pattern surface. The external electronic device 20 may determine the location and posture of the portable three-dimensional image measuring device 100 to which the marker 310 is attached, based on the formed pattern image.

The external electronic device 20 according to various embodiments may transform or align the coordinate system of the three-dimensional image of a surface of the patient P into the coordinate system of the external electronic device 20. For example, the external electronic device 20 may transform the coordinate system of the three-dimensional image of the surface of the patient P into the coordinate system of the external electronic device 20 based on the location and posture of the portable three-dimensional image measuring device 100 determined through the marker 310.

The external electronic device 20 according to various embodiments may transform or align the coordinate system of a medical image of the patient P, which is received from a medical device, to the coordinate system of the external electronic device 20. The external electronic device 20 according to various embodiments may perform image matching by unifying the coordinate systems between the three-dimensional image of the surface of the patient P and the medical image of the patient P.

Figure 8:
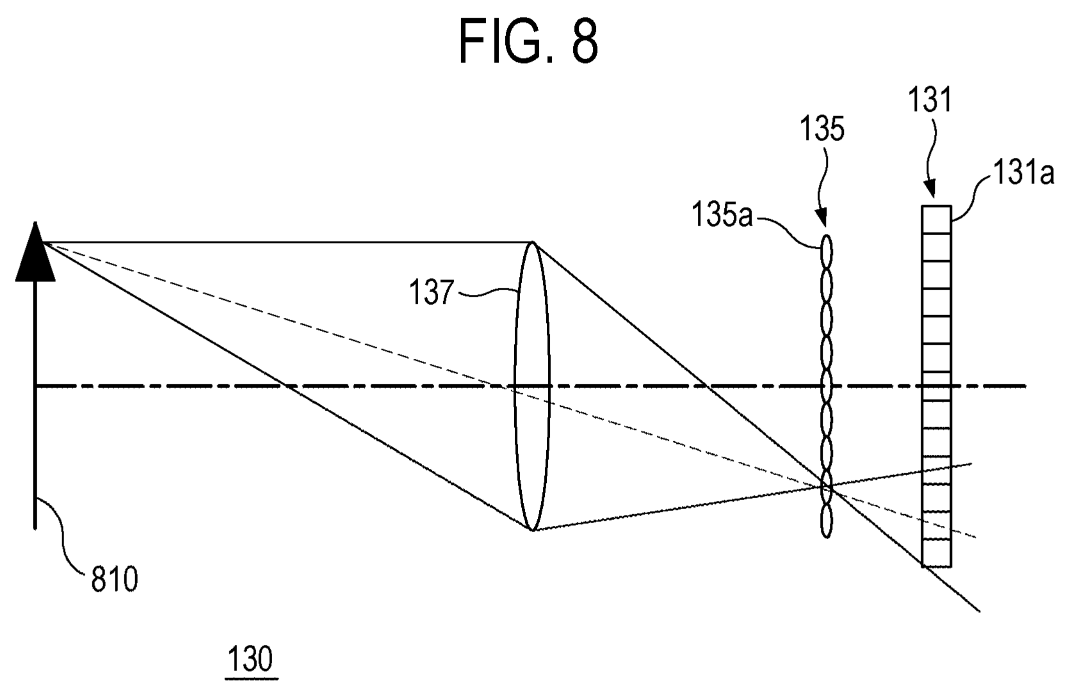
FIG. 8 is a view for explaining the structure of a camera according to various embodiments of the present disclosure.

FIG. 8 is a view for explaining a structure of the camera 130 according to various embodiments of the present disclosure.

Referring to FIG. 8, the camera 130 may include a condensing lens 137, a lens array 135, and an image sensor 131 sequentially disposed from an object 810. The camera 130 is an example of an arrangement structure for acquiring a light field image, but it may, of course, have a structure different from the depicted structure for acquiring the light field image.

The condensing lens 137 according to various embodiments is a component that condenses reflected light reflected from the object 810. The condensing lens 137 may be a convex lens with one focal length so that the reflected light reflected from the object 810 is condensed to one point. When the condensing lens 137 is implemented using a plurality of lenses, etc., the plurality of lenses may be defined as one thin lens according to a known thin lens theory. Accordingly, the diameter, focal length, and center of the condensing lens 137 may be respectively expressed as the diameter, focal length, and center of one thin lens defined in this way.

The lens array 135 according to various embodiments may disperse light entering through the condensing lens 137 and condense the light to a plurality of points formed at different locations. The lens array may be composed of a plurality of micro lenses. For example, the lens array 135 may be disposed closer to the condensing lens 137 than the focal length of the condensing lens 137. For example, the lens array 135 may be disposed farther from the condensing lens 137 than the focal length of the condensing lens 137.

The lens array 135 according to various embodiments may be disposed at a location corresponding to the focal length of the condensing lens 137. In this case, the focus of the light entering from the condensing lens 137 may be formed on one of a plurality of micro lenses 135*a*. In addition, the image sensor 131 may be fixedly installed at a location corresponding to the focal length of each micro lens 135*a* included in the lens array 135.

The image sensor 131 according to various embodiments may sense the light passing through the lens array 135. In addition, the image sensor 131 may acquire a light field image including a plurality of sub-images corresponding to the plurality of points. The image sensor 131 may include at least one imaging element of any type configured to acquire an imaging image of any object, and the image sensor 131 may be composed of a plurality of pixels 131*a*.

The image sensor 131 according to various embodiments may output, for example, a light field image having a format of photo aggregate file when photographing once. The photo aggregate file may include a plurality of sub-images having depths of different subjects in which the focal points of the object are formed at locations corresponding to the focal points of the plurality of micro lenses. Both color information and direction information of light may be stored in each sub-image according to X and Y coordinates.

The sub-images according to various embodiments may have different subject depths but may photograph the same object. The shapes of the object seen in the sub-images may be substantially the same, and a difference may occur between the locations of a clearly visible portion and a blurry portion. The clearly visible portion may be a portion where the focus of the corresponding micro lens 135*a* is formed and has the subject depth, and the blurry portion may be a portion excluding this.

The light field camera according to various embodiments may be configured to determine a subject depth posteriorly after photographing the object and combine images having different subject depths. Accordingly, the image sensor of the light field camera may have a posterior and variable subject depth. In addition, the light field image generated by the light field camera may include a plurality of sub-images that store both color information and direction information of light.

In another embodiment, the camera 130 may perform a refocusing process using a plurality of sub-images. In the refocusing process, an image having a desired depth may be newly extracted by combining a desired subject depth and color information of pixels corresponding to the optical path or direction calculated backward accordingly, among pixels of the light field image. Through this, it is possible to generate an image in which the irradiated pattern can be clearly identified.

Figure 9:
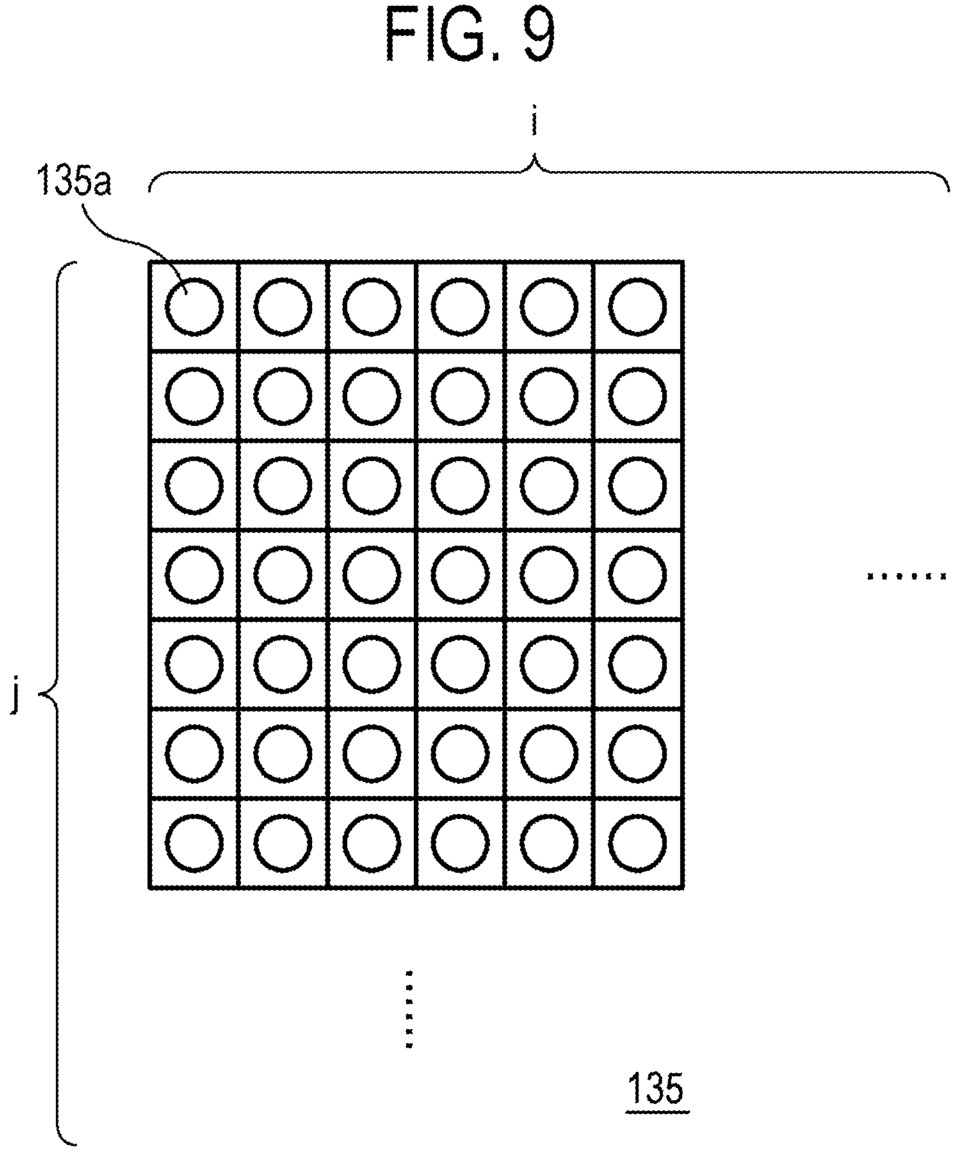
FIG. 9 is a view for explaining a lens array of the camera according to various embodiments of the present disclosure.

FIG. 9 is a view for explaining the lens array 135 of the camera 130 according to various embodiments of the present disclosure.

According to various embodiments, the plurality of micro lenses 135*a* included in the lens array 135 may be provided in N numbers (where N is a natural number of 1 or more). That is, N may mean a plurality. For example, in the lens array 135, i micro lenses may be disposed in each row and j micro lenses may be disposed in each column. Accordingly, N micro lenses may be composed of i*j matrices. For example, in order to form a more compact light field, the lens array 135 may have a shape in which approximately 1,000*1,000 micro lenses are arranged. The arrangement and number of micro lenses may vary according to various conditions (e.g., physical properties, photographing environment, required resolution of sub-images, or the number of pixels of an image sensor) of the condensing lens 137 and the micro lenses.

The plurality of N micro lenses according to various embodiments may disperse light entering through the condensing lens 137 into N points. The image sensor 131 shown in FIG. 8 may be divided into N areas corresponding to the N points formed by the N micro lenses. The focal points of the N micro lenses may be formed to be dispersed into the N areas of the image sensor 131.

According to various embodiments, when N sub-images are formed in the N areas, the light field image may include N sub-images having different subject depths. In addition, the processor may select an image having a subject depth at a predetermined location among the N images.

Figure 10:
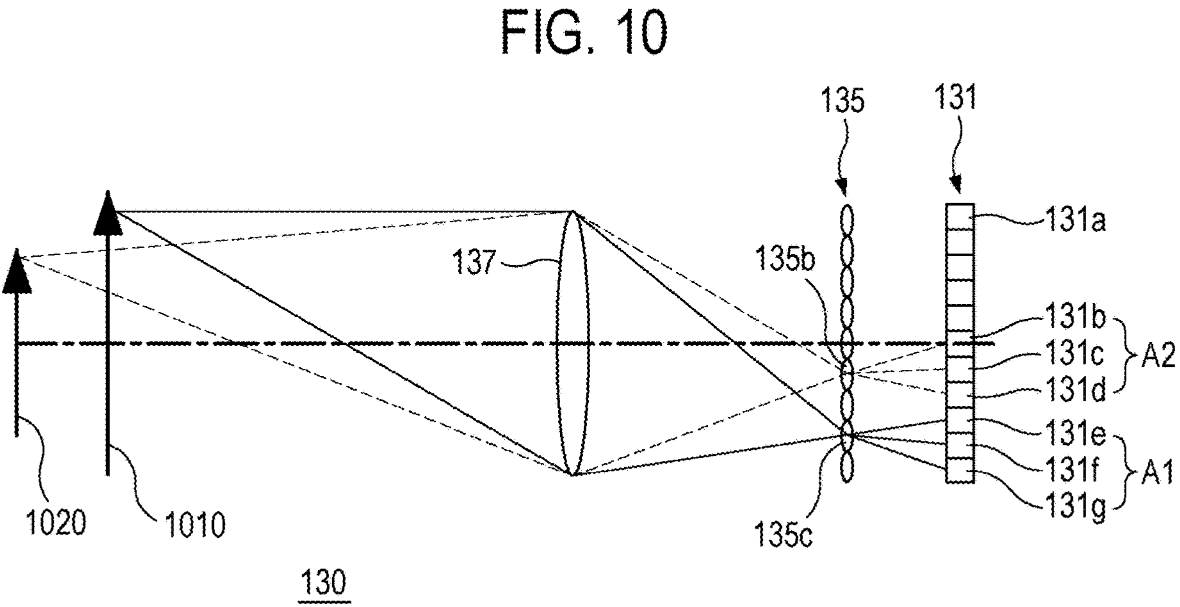
FIG. 10 is a view illustrating a process of forming different subject depths of a plurality of sub-images included in a light field image acquired by the camera according to various embodiments of the present disclosure.

FIG. 10 is a view showing a process of forming different subject depths of a plurality of sub-images included in the light field image acquired by the camera 130 according to various embodiments of the present disclosure.

The camera 130 according to various embodiments may include a condensing lens 137, a lens array 135, and an image sensor 131. A first object 1010 may be disposed closer to the condensing lens 137 than a second object 1020.

According to various embodiments, light emitted from the top of the first object 1010 may be condensed through the condensing lens 137 and focused on a micro lens 135*c* disposed on the lower side of the lens array 135. Light emitted from the micro lens 135*c* may reach an area A1 disposed on the lower side of the image sensor 131. Accordingly, the amount of light emitted from the top of the first object 1010 may be mainly distributed in the lower area A1 and a small amount of light may be distributed in the other areas. That is, an image of the top of the first object 1010 may be clearly formed on pixels 131*e*, 131*f*, and 131*g* included in the lower area A1.

According to various embodiments, light emitted from the top of the second object 1020 may be condensed through the condensing lens 137 and focused on the micro lens 135*b* in the middle of the lens array 135. Light emitted from the micro lens 135*b* may reach an area A2 disposed in the middle of the image sensor 131. Accordingly, the amount of light emitted from the top of the second object 1020 may be mainly distributed in the middle area A2 and a small amount of light may be distributed in the other areas. That is, an image of the top of the second object 1020 may be clearly formed on pixels 131*b*, 131*c*, and 131*d* included in the middle area A2.

Since a small amount of light emitted from the second object 1020 is distributed in the lower area A1, an image of the second object 1020 may be formed in a blurry state. In addition, since a small amount of light emitted from the first object 1010 is distributed in the middle area A2, an image of the first object 1010 may be formed in a blurry state. Accordingly, the lower area A1 may output a sub-image with a subject depth for the first object 1010, and the middle area A2 may output a sub-image with a subject depth for the second object 1020.

As described above, when an object is photographed by a camera according to various embodiments, a light field image including a plurality of sub-images having different subject depths may be generated.

Figure 11:
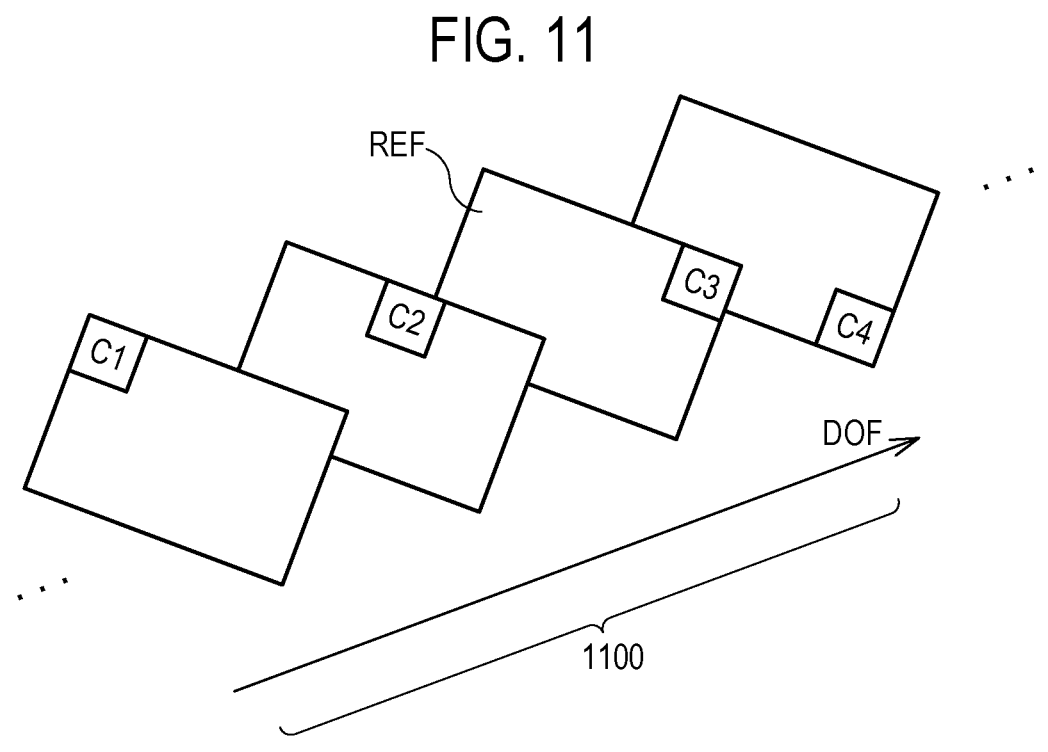

FIG. 11 is a view for explaining a light field image 1100 including a plurality of sub-images having different subject depths according to various embodiments of the present disclosure.

Referring to FIG. 11, the light field image 1100 according to various embodiments may be output as a photo aggregate file including a plurality of sub-images in which subject depths are formed in areas C1, C2, C3, and C4 at different locations in the image sensor 131. The plurality of areas C1, C2, C3, and C4 may be located at different locations within the sub-images, and depending on circumstances, at least two areas may be located at the same location. The photo aggregate file may have an aggregate format in which a plurality of sub-images physically separated from each other are simply collected. Unlike this, the photo aggregate file may be a format in which a plurality of sub-images are integrally combined with each other using a new extension method. According to various embodiments, the sub-images may include color information and direction information of light to have different subject depths. A direction of an arrow shown in FIG. 11 may represent a direction in which a distance at which a subject depth is to be formed increases.

While the foregoing methods have been described with respect to particular embodiments, these methods may also be implemented as computer-readable codes on a computer-readable recording medium. The computer-readable recoding medium includes any kind of data storage devices that can be read by a computer system. Examples of the computer-readable recording medium includes ROM, RAM, CD-ROM, magnetic tape, floppy disk, optical data storage device and the like. Also, the computer-readable recoding medium can be distributed to the computer systems which are connected through a network so that the computer-readable codes can be stored and executed in a distributed manner. Further, the functional programs, codes and code segments for implementing the foregoing embodiments can easily be inferred by programmers in the art to which the present disclosure pertains.

Although the technical spirit of the present disclosure has been described by the examples described in some embodiments and illustrated in the accompanying drawings, it should be noted that various substitutions, modifications, and changes can be made without departing from the scope of the present disclosure which can be understood by those skilled in the art to which the present disclosure pertains. In addition, it should be noted that that such substitutions, modifications and changes are intended to fall within the scope of the appended claims.

What is claimed is:

1. A portable three-dimensional image measuring device comprising:
- a light source configured to output patterned light;
- a camera configured to generate an image of an object by receiving reflected light generated by reflecting the patterned light from the object;
- an optical path control element configured to reflect the patterned light output from the light source so that the object is irradiated with the patterned light, and to transmit the reflected light reflected from the object so that the reflected light reaches the camera; and
- a processor,
- wherein an optical path of the patterned light output from the light source and irradiated onto the object and an optical path of the reflected light reflected from the object and reaching the camera overlap coaxially in a section between the optical path control element and the object, and
- wherein the processor is configured to:
  - measure a light intensity of reflected light at each of a plurality of points constituting a surface of the object using the image of the object acquired through the camera;
  - generate phase data based on the measured light intensity; and
  - generate a three-dimensional image of the surface of the object by calculating a height of each of the plurality of points based on the generated phase data.

2. The portable three-dimensional image measuring device of claim 1, wherein the image is a light field image in which a plurality of sub-images color information and direction information of the reflected light are combined.

3. The portable three-dimensional image measuring device of claim 1, further comprising a communication circuit,
- wherein the processor is configured to transmit the three-dimensional image of the surface of the object to an external electronic device through the communication circuit.

4. The portable three-dimensional image measuring device of claim 1, further comprising a marker installed to be movable from a predetermined location of the portable three-dimensional image measuring device,
- wherein the processor is configured to transmit information indicating displacement of the marker from the predetermined location to an external electronic device.

5. The portable three-dimensional image measuring device of claim 1, wherein the light source and the camera are disposed in a direction perpendicular to each other based on the optical path control element.

6. The portable three-dimensional image measuring device of claim 1, wherein the camera includes:
- a lens array in which a plurality of micro lenses are arranged; and
- an image sensor that captures the reflected light passed through the lens array.

7. The portable three-dimensional image measuring device of claim 1, wherein the light source includes:
- a pattern generator in which a plurality of patterns are formed; and
- an LED that irradiates the pattern generator with light.

8. The portable three-dimensional image measuring device of claim 7, wherein the light output by the LED is infrared light.

9. The portable three-dimensional image measuring device of claim 1, wherein the optical path control element is a transflective mirror.

10. The portable three-dimensional image measuring device of claim 1, further comprising:
- a first housing in which the light source, the camera, and the optical path control element are disposed; and
- a second housing coupled to the first housing and formed with an opening through which the object is irradiated with the patterned light output from the light source.

11. A three-dimensional image measuring method of a portable three-dimensional image measuring device, comprising:
- irradiating an object with patterned light output by a light source through an optical path control element; and generating an image of the object by receiving reflected light, which is generated by reflecting the patterned light from the object, by a camera through the optical path control element;

measuring a light intensity of reflected light at each of a plurality of points constituting a surface of the object using the image of the object acquired through the camera;

generating phase data based on the measured light intensity; and generating a three-dimensional image of the surface of the object by calculating a height of each of the plurality of points based on the generated phase data, wherein an optical path of the patterned light output from the light source and irradiated onto the object and an optical path of the reflected light reflected from the object and reaching the camera overlap coaxially in a section between the optical path control element and the object.

12. The three-dimensional image measuring method of claim 11, wherein the image is a light field image in which a plurality of sub-images color information and direction information of the reflected light are combined.

13. The three-dimensional image measuring method of claim 11, further comprising:

transmitting the three-dimensional image of the surface of the object to an external electronic device.

14. The three-dimensional image measuring method of claim 11, further comprising:

transmitting information indicating displacement of a marker, which is installed to be movable from a predetermined location of the portable three-dimensional image measuring device, from the predetermined location to an external electronic device.

15. The three-dimensional image measuring method of claim 11, wherein the light source and the camera are disposed in a direction perpendicular to each other based on the optical path control element.

16. The three-dimensional image measuring method of claim 11, wherein the camera includes:

a lens array in which a plurality of micro lenses are arranged; and an image sensor that captures the reflected light passed through the lens array.

17. The three-dimensional image measuring method of claim 11, wherein the light source includes:

a pattern generator in which a plurality of patterns are formed; and an LED that irradiates the pattern generator with light.

18. The three-dimensional image measuring method of claim 17, wherein the light output by the LED is infrared light.

19. The three-dimensional image measuring method of claim 11, wherein the optical path control element is a transflective mirror.

20. The three-dimensional image measuring method of claim 11, wherein the light source, the camera, and the optical path control element are disposed in a first housing, and wherein a second housing is coupled to the first housing and formed with an opening through which the object is irradiated with the patterned light output from the light source.

* * * * *